US009086398B1

(12) United States Patent
Gugaratshan et al.

(10) Patent No.: US 9,086,398 B1
(45) Date of Patent: Jul. 21, 2015

(54) ENGINE EXHAUST GAS SAMPLING FOR MASS SPECTROMETER REAL TIME OIL CONSUMPTION MEASUREMENT

(71) Applicant: Caterpillar Inc., Peoria, IL (US)

(72) Inventors: Kulasegaram Gugaratshan, Dunlap, IL (US); Orhan Altin, Denizli-Acipayam (TR); Joseph George Dewitt Chambers, Lafayette, IN (US); Eric Nathan Lucas, Washington, IL (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 14/159,903

(22) Filed: Jan. 21, 2014

(51) Int. Cl.
*G01N 33/28* (2006.01)
*H01J 49/26* (2006.01)
*H01J 49/00* (2006.01)
*G01M 15/10* (2006.01)

(52) U.S. Cl.
CPC ............ *G01N 33/28* (2013.01); *G01M 15/102* (2013.01); *H01J 49/0031* (2013.01); *H01J 49/26* (2013.01)

(58) Field of Classification Search
CPC ..... G01N 1/2202; G01N 31/12; G01N 33/28; H01J 49/4215; H01J 49/0009; H01J 49/0031; H01J 49/26; F02B 77/086; G01M 15/102
See application file for complete search history.

(56) References Cited

U.S. PATENT DOCUMENTS 4,321,056 A 3/1982 Dimitroff
4,372,155 A * 2/1983 Butler et al. ............... 73/114.72
5,415,025 A * 5/1995 Bartman et al. ............... 73/23.2
5,456,124 A 10/1995 Colvin
6,412,333 B2 7/2002 Inoue et al.
7,428,838 B2 * 9/2008 Gugaratshan et al. ......... 73/1.06
7,902,497 B2 * 3/2011 Gohl et al. .................... 250/282

FOREIGN PATENT DOCUMENTS

DE 19811788 9/1999
DE 102004053430 A1 * 5/2006 ............. G01N 27/62
DE 102009020360 A1 * 11/2010 ................ F01N 9/00
EP 1980724 3/2008

* cited by examiner

*Primary Examiner* — Michael Logie
(74) *Attorney, Agent, or Firm* — BakerHostetler

(57) ABSTRACT

An engine oil consumption measuring system includes a multi-cylinder engine with an exhaust system positioned in a test cell. A sampling probe has an end positioned in the exhaust system to receive exhaust. A sample transfer apparatus includes a first end fluidly connected to the sampling probe and a segment positioned in an interior of a furnace. A mass spectrometer includes a specimen probe with an inlet positioned in the segment of the sample transfer apparatus. A particulate filter is positioned in the segment of the sample transfer apparatus upstream from the inlet of the specimen probe. The sample transfer apparatus and the furnace are maintained at temperatures above an oil condensation temperature during testing.

20 Claims, 1 Drawing Sheet

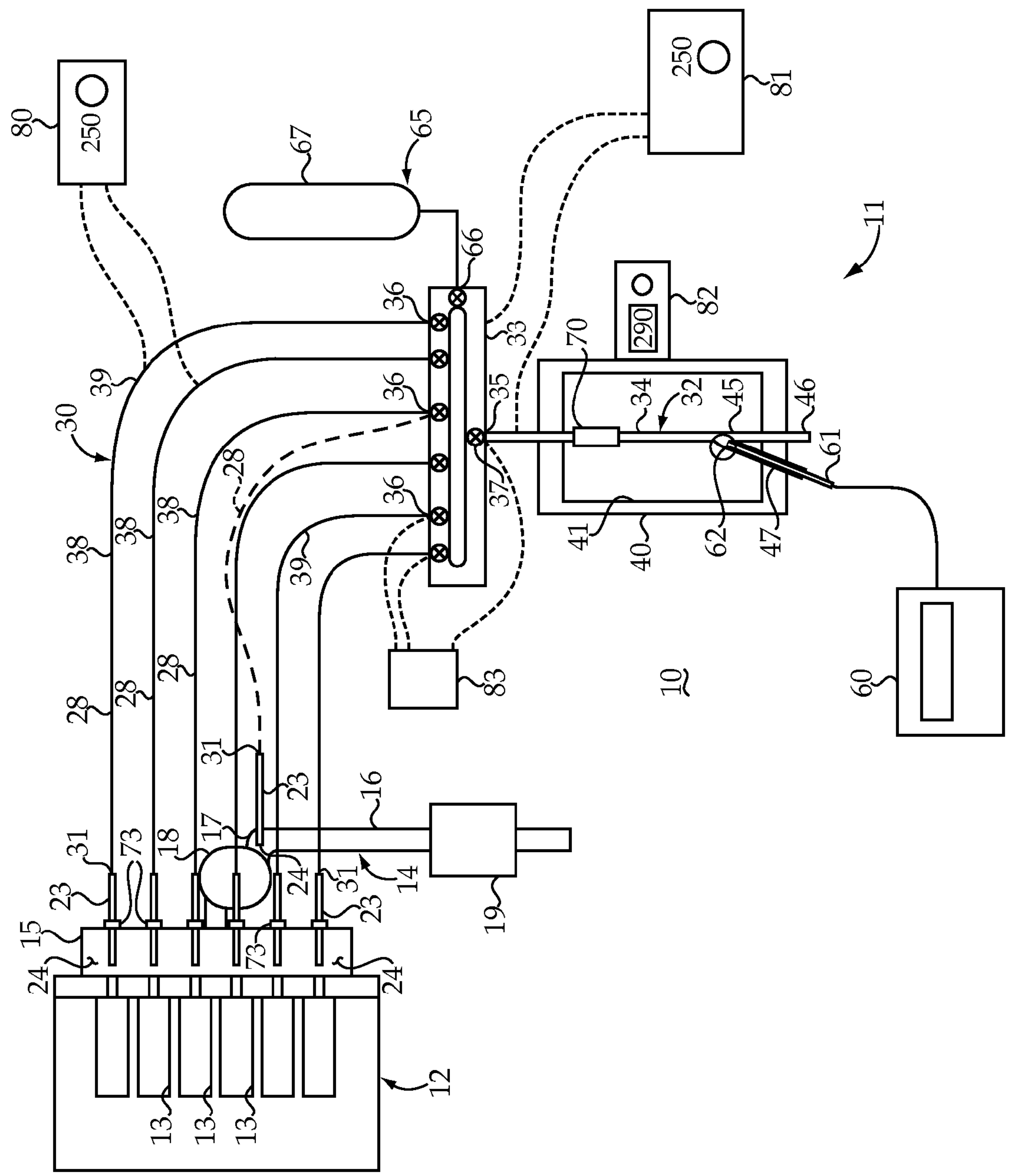
80
250
67
65
250
81
66
36
36
36
33
35
37
11
82
290
70
34
32
45
46
61
41
40
62
47
30
39
39
38
38
38
38
28
28
28
28
28
83
10
60
31
23
16
17
18
73
31
23
24
31
14
19
15
24
24
73
23
12
13
13
13

ENGINE EXHAUST GAS SAMPLING FOR MASS SPECTROMETER REAL TIME OIL CONSUMPTION MEASUREMENT

TECHNICAL FIELD

The present disclosure relates generally to measuring oil consumption of an internal combustion engine, and more particularly to a test cell system for accurately measuring oil consumption from one or more cylinders of an engine in real time.

BACKGROUND

Engine manufacturers have long evaluated engine designs and design changes by measuring engine oil consumption. In some instances, especially in the case of large engines, engine oil consumption may be measured by gravametric methods and withdraw methods that utilize an engine scale cart to measure engine oil consumption. These strategies can require a prolonged period of engine operation in order to obtain useful results. In addition, these traditional methods are unable to measure engine oil consumption for individual cylinders of a multi-cylinder engine. In an effort to overcome these problems, numerous non-traditional strategies for measuring engine oil consumption have been devised. For instance, U.S. Pat. No. 4,321,056 teaches a strategy for measuring engine oil consumption by analyzing the presence of zinc compounds in the engine exhaust responsive to engine oil that has added zinc compounds. In another example, European Patent EP1980724 teaches an engine oil consumption measuring device that senses sulfur dioxide compounds in the engine exhaust. These newer methods seek to infer engine oil consumption by measuring the presence of some other molecule as indirectly indicating oil consumption. Thus, these alternative methods suffer from problems associated with inaccuracies that can occur due to known and unknown reasons when indirectly measuring engine oil consumption based upon the presence of other tracer molecules in the engine exhaust.

The present disclosure is directed toward one or more of the problems set forth above.

SUMMARY

In one aspect, an engine oil consumption measuring system includes an engine with a plurality of cylinders and an exhaust system with an exhaust manifold fluidly connected to an exhaust pipe. A sampling probe has an end positioned in the exhaust system to receive exhaust. A sample transfer apparatus includes a first end fluidly connected to the sampling probe and a segment positioned in a heated interior of a furnace. A mass spectrometer includes a specimen probe with an inlet positioned in the segment of the sample transfer apparatus. A particulate filter is positioned in the segment of the sample transfer apparatus upstream from the inlet of the specimen probe.

In another aspect, a method of measuring engine oil consumption with an oil consumption measuring system includes a step of positioning a segment of a sample transfer apparatus in an interior of a furnace. A specimen probe of a mass spectrometer is positioned in the segment of the sample transfer apparatus. An end of a sampling probe is positioned in an exhaust system of an engine. The sample transfer apparatus is fluidly connected to the sampling probe. The sample transfer apparatus and the interior of the furnace are controlled to a temperature above an oil condensation temperature. An exhaust sample is moved from the exhaust system, into the sampling probe, through the sample transfer apparatus and into the specimen probe while the engine is running. Oil consumption of the engine is measured in real time by processing the exhaust sample with the mass spectrometer.

BRIEF DESCRIPTION OF THE DRAWINGS

FIG. 1 is a schematic of an engine oil consumption measuring system according to the present disclosure.

DETAILED DESCRIPTION

Referring to FIG. 1, a test cell 10, such as those used by engine manufacturers, houses an engine oil consumption measuring system 11 that includes an engine 12 with a plurality of cylinders 13. Engine 12 includes an exhaust system 14 with an exhaust manifold 15 fluidly connected to an exhaust pipe 16. Engine exhaust samples are gathered using sample probes 23 that include an end 24 positioned in the exhaust system 14 to receive exhaust. In the illustrated embodiment, a separate sampling probe 23 associated with each of the six engine cylinders has an end 24 positioned in exhaust manifold 15 so that each of the sample probes 23 can receive exhaust from a respective one of the plurality of cylinders 13. This multiple cylinder sampling set up may be used if individual cylinders are going to be measured or if a sensitivity type study is being requested. This installation may require that the exhaust manifold 15 be drilled at each cylinder location and a boss welded to the outer surface of the manifold. For instance, a swage lock fitting 73 may be welded to the manifold 15 at each cylinder location. The drilling locations and attachments of the swage lock fittings 73 might be oriented so that the sampling probe 23 enters into the head slightly and is pointed directly into the exhaust flow from that individual cylinder. The end 24 of each sample probe 23 may include on the order of about eight holes drilled sporadically about the last inch in length. These holes will help pull in an exhaust sample if the probe is not precisely in line with the flow.

A sample transfer apparatus 30 includes a first end 31 fluidly connected to the sampling probe(s) 23, and has a segment 32 positioned in the heated interior 41 of a furnace 40. Thus, the sample transfer apparatus 30 includes all of the hardware for transmitting the exhaust sample from sampling probe 23 to a specimen probe 61 of mass spectrometer 60. For multiple cylinder sampling, the sampling transfer apparatus 30 includes a plurality of sample lines 28 that each fluidly connect one of the sampling probes 23 to a heated switch box 33. Each of the sample lines 28 may be equipped with a line heater 38 in order to inhibit condensation of oil on the fluid passageways defined by the sample lines 28. These sample lines may be formed from a suitable non-reactive stainless steel tubing in order to further limit interaction between the sample transfer apparatus 30 and the exhaust samples being evaluated by the mass spectrometer 60. A transfer line 34 has one end 35 fluidly connected to the heated switch box 33, and includes the segment 32 positioned in the heated interior 41 of furnace 40.

Depending upon the specific heating strategies utilized, at least one controller is in control communication with the line heaters 38, the heated switch box 33 and furnace 40, and are configured to maintain the respective sample lines 38, heated switch box 33 and the interior 41 of furnace 40 above an oil condensation temperature. For instance, the illustrated embodiment shows a first controller 80 maintaining line heaters 38 and in turn sample lines 28 at about 250° C., which is well above an oil condensation temperature associated with a 5W-40 lubricating oil used for a diesel engine. Likewise, a second controller 81 may maintain heated switch box 33 and a portion of transfer line 34 above 250° C. Finally, furnace 40 may include its own controller 82, and may be set to a slightly higher temperature may be on the order of 290° C. for maintaining the interior 41 of furnace 40 well above oil condensation temperatures. Those skilled in the art will appreciate that skilled artisans can determine the appropriate temperature depending upon what oil is used by the engine 12, which may or may not be a diesel engine. The line heaters 38 and the heater used for a portion of transfer line 34 may be a suitable heat wrap or heat tape the type well known in the art. Furthermore, it might be desirable to wrap the junction of each individual sample probe 23 with the swage lock fitting 73 with appropriate heated tapes or insulation to avoid any cold spots in the sample transfer apparatus 30.

The heated switch box 33 may include a plurality of heated valves 36 that are each positioned to open or close one of the sampling lines 28 to the transfer line 34. Heated switch box 33 may also include a separate heated control valve 37 at the outlet from heated switch box 33, and may also include a separate heated flush valve 66. In order to remove carbon and other particles that could undermine proper operation of the system, a particulate filter 70 is positioned in the segment 32 of transfer line 34 upstream from the inlet 62 of specimen probe 61. Thus, both the particulate filter 70 and the inlet 62 of specimen probe 61 are positioned in the heated interior 41 of furnace 40. In one specific example, the particulate filter 70 may comprise a quartz wool filter of a type well known in the art.

The engine oil consumption measuring system 11 may also include a flush system 65 fluidly connected to heated switch box 33 at a flush valve 66. Flush system 65 may include a source of pressurized non-reactive gas 67. The non-reactive gas may be nitrogen and be maintained in the range of 15 to 20 PSI or more depending upon the size of the engine 12 being tested. By properly opening different ones of valves 36, 37 and 66, the sample transfer apparatus 30 may be flushed in both directions, namely in the direction of outlet pipe 46 and in the direction of engine 12 for proper conditioning and purging of the system for clean operation. It has been observed that the best results are achieved when beads 39 in sample lines 28 are maintained with at least a radius of one foot. Proper support of the sample lines 28 may, for instance, be buttressed in this regard by utilizing twist ties or the like to avoid small radius beads that could undermine performance.

So that no substantial back pressure is placed upon the sample transfer apparatus 30, transfer line 34 may be constructed from a suitable non-reactive stainless steel tubing to include a Y-branch 45 that divides transfer line 34 into an outlet pipe 46 and a specimen pipe 47. As shown, the specimen probe 61 is received in specimen pipe 47 so that inlet 62 is positioned in heated interior 41 of furnace 40.

The sample transfer apparatus 30 may also be configured for total exhaust sampling by positioning a sample probe 23 in exhaust pipe 16. Good results have been obtained by positioning the total exhaust sampling probe 23 in an elbow section 17 of a exhaust pipe 16 downstream from a turbocharger 18, but upstream from a diesel particulate filter 19. Thus, elbow section 17 within which the total exhaust sampling probe 23 is positioned is itself fluidly positioned between the turbocharger 18 and the diesel particulate filter. In the illustrated embodiment, this sampling probe 23 is shown fluidly connected with a sampling line 28 (dashed line) to a middle heated valve 36 of heated switch valve 33. Nevertheless, those skilled in the art will appreciate that if only total exhaust sampling as being performed, the heated switch box 33 of the sample transfer apparatus 30 may be omitted in favor of a more direct connection to transfer line 34. However, it may be desirable to continue using switch box 33 even when doing total exhaust sampling since the system may still need flushing using flush system 65 in order to obtain accurate results. Access to the exhaust pipe 16 again may be gained through a drilling and attachment thereto with a boss or swage lock fitting 73 so that sample probe 23 can be inserted directly into the exhaust flow preferably toward the center or middle area of the exhaust pipe 16. The total exhaust sampling set up shown in configured to determine oil consumption for the engine 12 plus turbocharger 18. Good results for a total exhaust sampling have been obtained by positioning the sample probe 23 a short distance downstream from turbocharger 18, but definitely upstream from any diesel particulate filter 19 or diesel oxidation catalyst which may be coated on the filter. Those skilled in the art will appreciate that the various heated valves 36, 37 and 66 may be electronically controlled by a separate controller 83 in a manner known in the art.

INDUSTRIAL APPLICABILITY

The present disclosure is generally applicable to real time testing of engine oil consumption from an internal combustion engine. The present disclosure finds specific applicability to real time engine oil consumption of large diesel engines.

In order to obtain good quality results, several practices might be performed before actually initiating a test. For instance, the engine oil might be changed and the oil filter switched. In addition, the right volume of oil in the sump should be assured, since running the engine oil level too low or too high can cause inaccurate oil consumption data. The quartz wool particulate filter 70 might need to be changed after only running engine 12 for several hours. In other words, the quartz wool mesh particulate filter 70 may become filled with soot rather quickly, and therefore should be changed often in order to avoid flow restrictions and back pressure that could undermine results. Well before actually running a test, all of the sample lines 28, furnace 40 and heated switch box 33 should have ample time to come up to their operating temperatures, which may be maintained on the order of 250° C. to about 290° C. in the case of a large diesel engine. It should also be noted that the filament for the mass spectrometer 60 may take several hours to stabilize and stop drifting prior to testing. Therefore, the mass spectrometer 60 might be turned on long before attempting to calibrate or take data. If background noise drifts more than lkc over a period of about 20 minutes, the system may be in need of flushing as this may indicate that too much drift is occurring to obtain good data. Another good practice might be to run a daily check point at a rated engine condition and compare the performance and PCM parameters to make sure that the engine is running similar while also checking the turbocharger 18, oil, water, boost as well as intake manifold pressure and temperature. In addition, these daily checks might include ensuring that main timing, and injection pilot and post timing, rail pressure and EGR are all as per specifications. Another good practice might be to pay attention to the EI source pressure in the mass spectrometer, especially during testing. A sudden drop below 40 mtorr means that the system might be getting dirty and the capillary in the specimen probe 61 is likely plugged. Sometimes, adjusting the vacuum controller of the mass spectrometer 60 repeatedly up and down may clean the capillary of specimen tube 61. In general, data should be taken as quickly as possible, such as within a few hours of the last calibration.

To do otherwise could invite drift to play a large and undesirable roll in the data quality. In general, sample probes 23 should not be left in the engine when those cylinders are not being tested. For instance, a sample probe 23 could vibrate and break off in the engine if left for an extended amount of time.

The use of the flushing system 65 allows for the establishment of a baseline prior to a test by closing valves 36, opening valves 66 and 37 and confirming that the reading of the mass spectrometer 60 is at an expected baseline. Deviations from that baseline could indicate dirt, condensed oil or some other contaminate is in the system requiring a more thorough flushing. Reverse flushing can also be accomplished by closing valve 37 and selectively opening one or more of the valves 36 to push nitrogen in a reverse direction toward engine 12 prior to actual testing.

In general, measuring engine oil consumption with an oil consumption measuring system 11 includes positioning a segment 32 of a sample transfer apparatus 30 in a heated interior 41 of a furnace 40. A specimen probe 61 of a mass spectrometer 60 is also positioned in the segment 32 of sample transfer apparatus 30. The end 24 of a sampling probe 23 is positioned in an exhaust system 14 of engine 12. For instance, a multi-cylinder testing, the sampling probes 23 would be positioned in the exhaust manifold 15 as shown, whereas total oil consumption might be accomplished by positioning a single sampling probe 23 in an elbow section 17 of exhaust pipe 16. The sample transfer apparatus 30 is then fluidly connected to the sampling probe(s) 23, such as via one or more sample lines 28. A temperature of the sample transfer apparatus 30 and the interior 41 of furnace 40 are then controlled to be maintained above an oil condensation temperature, such as in the range 250° C. to 290° C., for example. An exhaust sample is moved from the exhaust system 14, into the sampling probe 23, through the sample transfer apparatus 30 and into the specimen probe 61 while engine 12 is running. Thus, during multiple cylinder sampling, only one of the heated valves 36 may be opened at any given instance. Real time measuring of engine oil consumption of engine 12 is accomplished by processing the exhaust sample with the mass spectrometer 60.

The method of measuring engine oil consumption may also include preparing the oil consumption measuring system 11 for receiving an exhaust sample. This preparation may include the following steps in order by initially closing the sample transfer apparatus 30 to the exhaust system 14, such as by closing valves 36. Next, the sample transfer apparatus 30 may be flushed with the non-reactive gas (e.g. nitrogen) originating from source 67 by opening valve 66. A flushing sample is then moved into the specimen probe 61. Mass spectrometer results for the flushing sample may be compared to a pre-determined baseline. The pre-determined baseline may be established prior to moving an exhaust sample into any of the sampling probes 23. The sample transfer apparatus 30 may be closed to the source of non-reactive gas 67 by closing valve 66 after performing the preparation steps identified above. Those skilled in the art will appreciate that gathering an exhaust sample for a mass spectrometer 60 includes opening the sample transfer apparatus 30 to the exhaust system 14 by opening one or more of the heated valves 36. During testing, particles in the exhaust sample are trapped with the particulate filter 70 that is positioned in the heated interior 41 of furnace 40.

Those skilled in the art will appreciate that the heated switch box 33 includes a plurality of heated valves 36 that are each positioned to open and close one of the sampling lines 28 to the transfer line 34. When evaluating oil consumption for a single one of the engine cylinders 13, exactly one of the heated valves 36 will be opened and the remaining heated valves 36 closed. One can switch between different engine cylinders 13 by opening a different one of the heated valves 36 and maintaining the remaining heated valves 36 closed. When in operation, the Y-branch 45 divides the transfer line 34 into an outlet pipe 46 and a specimen pipe 47. The specimen probe 61 is positioned in the specimen pipe 47 so as not to create back pressure by the probe 61 reducing the flow area in transfer line 34. As stated earlier, better results have been obtained by maintaining each bend 39 in each of the sample lines 28 to a radius greater than one foot. During multiple cylinder testing, the preparation steps outlined above may be performed before gathering data on each successive different cylinder. In other words, the system 11 may benefit from flushing between the opening and closure of each different heated valve 36.

By taking the exhaust sample closer to the actual exhaust valve of engine 12, and transferring the sample via heated lines and heated switch box, better quality data can be obtained. In addition, by positioning the particulate filter 70 and the specimen probe 61 in the heated interior 41 of furnace 40, oil condensation that could also undermine data accuracy may be avoided. In addition, removing carbon and other particles can also leverage the system to provide good quality data.

The solution taught by the present disclosure addresses problems generally associated with the fact that small streams of exhaust samples can cool down relatively fast resulting in hydrocarbon (oil) condensation rather quickly that could undermine data. In addition, exhaust soot particles will get into the sample line, but are trapped prior to entry into the specimen probe 61 in order to avoid undermining data. The present strategy also allows for taking samples from every cylinder of relatively large engines, which has been extremely difficult in the past. In addition, the system 11 of the present disclosure allows for the provision of a steady stream exhaust flow rate to the mass spectrometer 60, and allows for quickly switching among different engine cylinders 13. The set up of the present disclosure also allows the same system 12 to be reconfigured between multiple cylinder sampling and total engine exhaust sampling simply by relocating a sample probe 23 and changing a connection to heated switch box 33.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. An engine oil consumption measuring system comprising:

an engine with a plurality of cylinders and an exhaust system with an exhaust manifold fluidly connected to an exhaust pipe;

a sampling probe with an end positioned in the exhaust system to receive exhaust;

a furnace having a heated interior;

a sample transfer apparatus that includes a first end fluidly connected to the sampling probe and a segment positioned in the interior of the furnace;

a mass spectrometer that includes a specimen probe with an inlet positioned in the segment of the sample transfer apparatus; and a particulate filter positioned in the segment of the sample transfer apparatus upstream from the inlet of the specimen probe.

2. The engine oil consumption measuring system of claim 1 wherein the sampling probe is one of a plurality of sampling probes that each have one end positioned in the exhaust manifold for receiving exhaust from a respective one of the plurality of cylinders;

the sample transfer apparatus includes a plurality of sample lines that each fluidly connect one of the sampling probes to a heated switch box, and a transfer line with one end fluidly connected to the heated switch box and the segment positioned in the interior of the furnace;

wherein the heated switch box includes a plurality of heated valves, each positioned to open or close one of the sampling lines to the transfer line.

3. The engine oil consumption measuring system of claim 2 wherein each of the sample lines includes a line heater; and at least one controller in control communication with the line heaters, the heated switch box and the furnace, and being configured to maintain the respective sample lines, the heated switch box and the interior of the furnace above an oil condensation temperature.

4. The engine oil consumption measuring system of claim 3 including a flush system fluidly connected to the heated switch box at a flush valve, and including a source of pressurized non-reactive gas.

5. The engine oil consumption measuring system of claim 4 wherein the segment of the transfer line includes a Y branch that divides the transfer line into an outlet pipe and a specimen pipe.

6. The engine oil consumption measuring system of claim 5 wherein each of the sampling probes extends through a swage lock fitting welded to the exhaust manifold;

each of the sampling lines and the transfer line includes a non-reactive stainless steel tube; and the non-reactive gas is nitrogen.

7. The engine oil consumption measuring system of claim 6 wherein each bend in each of the sample lines has a radius greater than one foot.

8. The engine oil consumption measuring system of claim 1 wherein the sampling probe has an end positioned in an elbow section of the exhaust pipe.

9. The engine oil consumption measuring system of claim 8 wherein the engine includes a turbocharger, and the exhaust system includes a diesel particulate filter;

the elbow section is fluidly positioned between the turbocharger and the diesel particulate filter.

10. A method of measuring engine oil consumption with an oil consumption measuring system, comprising the steps of:

positioning a segment of a sample transfer apparatus in an interior of a furnace;

positioning a specimen probe of a mass spectrometer in the segment of the sample transfer apparatus;

positioning an end of a sampling probe in an exhaust system of an engine;

fluidly connecting the sample transfer apparatus to the sampling probe;

controlling a temperature of the sample transfer apparatus and the interior of the furnace above an oil condensation temperature;

moving an exhaust sample from the exhaust system, into the sampling probe, through the sample transfer apparatus and into the specimen probe while the engine is running; and real time measuring oil consumption of the engine by processing the exhaust sample with the mass spectrometer.

11. The method of claim 10 including a step of preparing the oil consumption measuring system for receiving an exhaust sample;

the preparing step includes:

closing the sample transfer apparatus to the exhaust system;

flushing the sample transfer apparatus with a non-reactive gas;

moving a flushing sample into the specimen probe; and comparing mass spectrometer results of the flushing sample to a predetermined baseline.

12. The method of claim 11 including a step of establishing the predetermined baseline prior to the step of moving the exhaust sample.

13. The method of claim 12 including the steps of closing the sample transfer apparatus to a source of non-reactive gas after performing the preparation step; and opening the sample transfer apparatus to the exhaust system.

14. The method of claim 13 including a step of trapping particles in the exhaust sample with a particulate filter positioned in the interior of the furnace.

15. The method of claim 14 wherein the sampling probe is one of a plurality of sampling probes that each have one end positioned in an exhaust manifold of the exhaust system for receiving exhaust from a respective one of a plurality of cylinders;

the sample transfer apparatus includes a plurality of sample lines that each fluidly connect one of the sampling probes to a heated switch box, and a transfer line with one end fluidly connected to the heated switch box and the segment positioned in the interior of the furnace;

wherein the heated switch box includes a plurality of heated valves, each positioned to open or close one of the sampling lines to the transfer line; and the step of moving the exhaust sample includes opening exactly one of the heated valves.

16. The method of claim 15 wherein the segment of the transfer line includes a Y branch that divides the transfer line into an outlet pipe and a specimen pipe; and the specimen probe is positioned in the specimen pipe.

17. The method of claim 16 includes maintaining each bend in each of the sample lines to a radius greater than one foot.

18. The method of claim 17 including the steps of:

closing the exactly one of the heated valves;

performing the preparing step;

opening exactly one of the other heated valves.

19. The method of claim 14 wherein the sampling probe has an end positioned in an elbow section of an exhaust pipe of the exhaust system.

20. The method of claim 19 wherein the engine includes a turbocharger, and the exhaust system includes a diesel particulate filter;

the elbow section is fluidly positioned between the turbocharger and the diesel particulate filter.

* * * * *